United States Patent [19]

Jahanger

[11] Patent Number: 4,870,965
[45] Date of Patent: Oct. 3, 1989

[54] UMBILICAL CORD CUTTING AND CLAMPING DEVICE

[76] Inventor: Mohammed S. Jahanger, 500 Egg Harbor Rd., Turnersville, N.J. 08012

[21] Appl. No.: 164,447

[22] Filed: Mar. 4, 1988

[51] Int. Cl.⁴ ............................................. A61B 17/32
[52] U.S. Cl. .................................... 128/318; 128/325; 128/346
[58] Field of Search ............... 128/305, 311, 318, 346, 128/325, 321, 322, 326; 604/22; 30/131, 134; 7/131, 135

[56] References Cited

U.S. PATENT DOCUMENTS

| | | |
|---|---|---|
| 640,517 | 1/1900 | Acheson . |
| 2,052,870 | 9/1936 | Coco . |
| 2,060,724 | 11/1936 | Carroll . |
| 2,384,697 | 9/1945 | Riccardi . |
| 3,006,344 | 10/1961 | Vogelfanger . |
| 3,155,071 | 6/1963 | Mayer . |
| 3,503,398 | 3/1970 | Fogarty et al. ...................... 128/346 |
| 3,631,858 | 7/1972 | Ersek . |
| 3,783,875 | 1/1974 | Winshel . |
| 3,921,640 | 11/1975 | Freeborn . |
| 3,981,308 | 9/1976 | Schlein ................................ 128/346 |
| 4,390,019 | 6/1983 | Le Veen et al. .................... 128/325 |
| 4,428,374 | 1/1984 | Auburn ........................... 128/346 X |
| 4,434,795 | 3/1984 | Mericle . |
| 4,572,181 | 2/1986 | Mattler . |
| 4,602,629 | 7/1986 | Schnirman . |
| 4,671,282 | 6/1987 | Tretbar . |
| 4,672,966 | 6/1987 | Haas ................................... 128/330 |

FOREIGN PATENT DOCUMENTS 934296 8/1963 United Kingdom ................ 128/318

Primary Examiner—Michael H. Thaler
Attorney, Agent, or Firm—Paul and Paul

[57] ABSTRACT

An umbilical cord cutting and clamping device simultaneously severs an umbilical cord to form a maternal cord end and fetal cord end and releasably clamps the maternal cord end. A separate fetal cord end clip mounted in the device simultaneously secures the fetal cord end. The fetal cord end clamp is ejected automatically from the device after the fetal cord end has been clipped. The device provides a more uniform application of clamping force to the umbilical cord than scissors-like devices thereby reducing undesirable hemorrhaging from the clamped cord ends. The device can be used to clamp securely umbilical cords having a large variation in diameter.

20 Claims, 2 Drawing Sheets

UMBILICAL CORD CUTTING AND CLAMPING DEVICE

BACKGROUND OF THE INVENTION

1. Field of the Invention

The present invention relates generally to obstetrical instruments and more particularly to a device for simultaneously cutting and clamping an umbilical cord and to clips for use in combination with the device.

2. Brief Description of Prior Art

Surgical instruments for simultaneously severing and clamping the umbilical cord of a newborn infant are known. For example, U.S. Pat. Nos. 640,517, 2,052,870, 2,060,724, 3,166,071, and 4,428,374 each disclose clamping devices for simultaneously cutting the umbilical cord and clamping both the maternal and the fetal ends of the severed cord. The devices generally employ a pair of clamps which are detachable or removable from the clamping device after the cord has been severed and clamped. These devices generally have a simple scissors-like configuration, the force manually exerted by an operator on the handle of the clamping device being transmitted through a single pivot or fulcrum to the clamping and severing means.

U.S. Pat. No. 3,631,858 discloses a device or a device for simultaneously clamping and severing the umbilical cord in a single operation requiring only one hand, no detachable clamps being employed.

U.S. Pat. No. 4,648,401 discloses a scissors-like surgical instrument for severing an umbilical cord employing a single umbilical cord clamp and a single-use, disposable blade assembly to sever the cord. The instrument permits the release of the clamp or hemostat on the maternal end of the umbilical cord immediately after the cord is cut for collection of a blood specimen for a fetal Rh factor screen test to avoid discomforting the infant by obtaining the specimen directly from the infant.

In general it is desirable in obstetrical practice to sever and securely clamp both ends of the severed umbilical cord as quickly as possible. This is especially so when complications arise during the delivery such as when the umbilical cord is wrapped around the infant's neck. The fetal end of the severed cord must be securely clamped so that during the drying and consequent shrinkage of the cord which occurs after delivery further bleeding, infection, or umbilical hernia do not occur.

The prior art devices generally share a common disadvantage in that they are adapted for use in severing and clamping umbilical cords having a relatively small diameter. However, in obstetrical practice the range in diameter of the umbilical cords encountered is substantial (e.g., about 1–2.5 cm), and the prior art devices are generally not suitable for severing and clamping cords having relatively large diameters. As umbilical cords include tough, gelatinous, fibrous tissue (Wharton's jelly), as well as two arteries and a vein, scissors-like devices may not provide sufficient force to cleanly sever them. Further, the scissors-like prior art severing and clamping devices apply severing and clamping forces to the cord which vary inversely with the distance from the fulcrum or pivot point. This manner of applying forces to the cord can cause substantial problems, especially when large diameter cords are to be cut and clamped. For example, the force applied to clamp the cord proximate the fulcrum of the device can exceed the force required to tear or cut the cord, thereby permitting hemorrhaging of the cord adjacent to the clamp end. Similarly, the force applied to clamp the portion of cord furthest removed from the fulcrum of a scissors-like device may be insufficient to securely clamp the cord, thereby providing the same undesired result.

Thus, there is a need for a surgical instrument for severing and clamping the umbilical cord of substantially varying diameter while simultaneously avoiding the application of excessive force which would otherwise damage the clamped cord resulting in undesired bleeding and/or which tends to clamp a portion of the cord with insufficient force thereby permitting bleeding through the insufficiently clamped severed cord end.

Further, there is a need for a surgical instrument which can minimize the time which an obstetrician must expend in cutting and securely clamping the ends of the umbilical cord during delivery.

SUMMARY OF THE INVENTION

The present invention provides an umbilical cord cutting and clamping device for severing an umbilical cord to form a maternal cord end and a fetal cord end, and for clamping the maternal cord end and the fetal cord end. The device is adapted for use with a fetal cord end clip. Advantageously, the invention provides a physician with means for quickly severing an umbilical cord and securely clamping both cord ends, thereby reducing risks associated with hemorrhaging of the cord ends and infection.

The device comprises a lower assembly including a lower jaw and a lower handle means. The lower jaw includes a lower clamping member for clamping the maternal cord end, a lowering severing member for severing the umbilical cord, and lower support means for supporting and positioning the fetal cord end clip.

The device further comprises an upper jaw including an upper clamping member for clamping the maternal cord end, an upper severing member for severing the umbilical cord, and an upper support means for supporting and positioning the fetal cord end clip. The upper jaw is pivotally affixed to a lower assembly and adapted to be pivoted from an open position for admitting an umbilical cord between the upper jaw and the lower jaw and a closed position for severing and clamping the umbilical cord.

The device further comprises an upper handle means which is pivotably affixed to the upper jaw, and lever means pivotably affixed to the upper handle means and the lower handle means. The distance between the upper jaw-lower assembly pivot and the lower assembly-lever means pivot is greater than the distance between the upper jaw-upper handle means pivot and the upper handle means-lever means pivot. In addition, the distance between the lower assembly-upper jaw pivot and the upper jaw-upper handle means pivot is less than the distance between the upper handle means-lever means pivot and the lower assembly-lever means pivot. Thus, as the device is closed, the upper jaw-upper handle pivot moves in an arc about the upper jaw-lower assembly pivot. This arrangement advantageously provides a more uniform application of clamping force through the umbilical cord as the device is closed than do prior art scissors-type severing and clamping devices.

Preferably, the device of the present invention has maternal cord end clamping means which is adapted to deform as the maternal cord end is clamped to at least partially conform to the clamped maternal cord end. This feature of the present invention also advantageously contributes to a more uniform application of force to the umbilical cord to be clamped than provided by prior art devices. In one presently preferred embodiment of the invention, an elongated aperture is formed in the lower jaw, the aperture being sized and positioned to allow the lower jaw clamping member to deform as the maternal cord end is clamped as the device is closed. Preferably, the fetal cord end clip is also provided with at least one such aperture for a like purpose.

The lower severing member and the upper severing member together comprise a severing means cooperating to sever an umbilical cord positioned therebetween when the device is closed. Similarly, the upper clamping member and lower clamping member together comprise a maternal cord end clamping means and cooperate to clamp the maternal cord end when the device is closed. Preferably, the maternal cord end clamping means is generally parallel and spaced from the severing means. In one presently preferred embodiment of the invention the maternal cord end clamping means is spaced by at least about 3 millimeters from the severing means.

In the present invention the upper and lower support means together comprise means for supporting and positioning the fetal cord end clamping means when the device is open and as the device is closed and the fetal cord end is clamped. Preferably, the device also advantageously includes means for releasing the fetal cord end clamping means from the device as the device is closed and after the fetal cord end has been clamped. In a presently preferred embodiment of the invention the release means comprises a cam member mounted in the lower jaw.

It is preferred that the support members be adapted to position the fetal cord end clamping means generally parallel and spaced from the severing means of the device. In a presently preferred embodiment, the fetal cord end clamping means is spaced by at least about 3 millimeters from the severing means of the device.

In a presently preferred embodiment of the invention the fetal cord end clamping means has a pair of elongated arms extending radially from a generally arcuate central section having an opening formed therein for receiving a support member of the device. Each of the arms of the fetal cord end clamping means has a generally straight inner surface and has teeth formed thereon for contacting the umbilical cord surface. At least one of the arms preferably has an elongated aperture formed therein for cushioning the force exerted on an umbilical cord end when the clip is closed thereon. Lock means are formed proximate the ends of the clamp arms locking the arms together when the clip is closed about an umbilical cord end. The arms of the open clamping means form an acute angle such that the clamp arms must be slightly compressed together against the spring-like force exerted by the generally arcuate central section of the clamping means when the fetal cord end clamping means is mounted in a fully opened cutting and clamping device. Preferably, the clamping means is mounted in the device in a manner which facilitates its release by the release means after the device is closed and the fetal cord end has been clamped.

The present invention advantageously provides the obstetrician with a means of accomplishing in less than a second a series of procedures (cutting the umbilical cord and clamping the cord ends) which could otherwise take as long as five or six minutes. This permits the physician to act quickly, an important advantage during medical crises, as when a Caesarian section is being performed because of fetal heart distress caused by looping of the umbilical cord around the neck of the infant, or other complications. In such cases even a few seconds delay in cutting the umbilical cord may be fatal to the infant. The device and associated clip also help prevent bleeding of the cut cord ends and infection.

Because the device of the present invention can be easily constructed to be disposable after a single use, additional protection can be provided to the obstetrician, other medical personnel and other patients including newborn infants when an infant has been delivered by a mother known or suspected to be suffering from an infectious disease such as AIDS.

Other objects and advantages of the present invention will become readily apparent to those skilled in the art from a reading of the following brief description of the drawings, the detailed description of the preferred embodiments, and the appended claims.

DETAILED DESCRIPTION OF THE PREFERRED EMBODIMENTS

Figure 1:
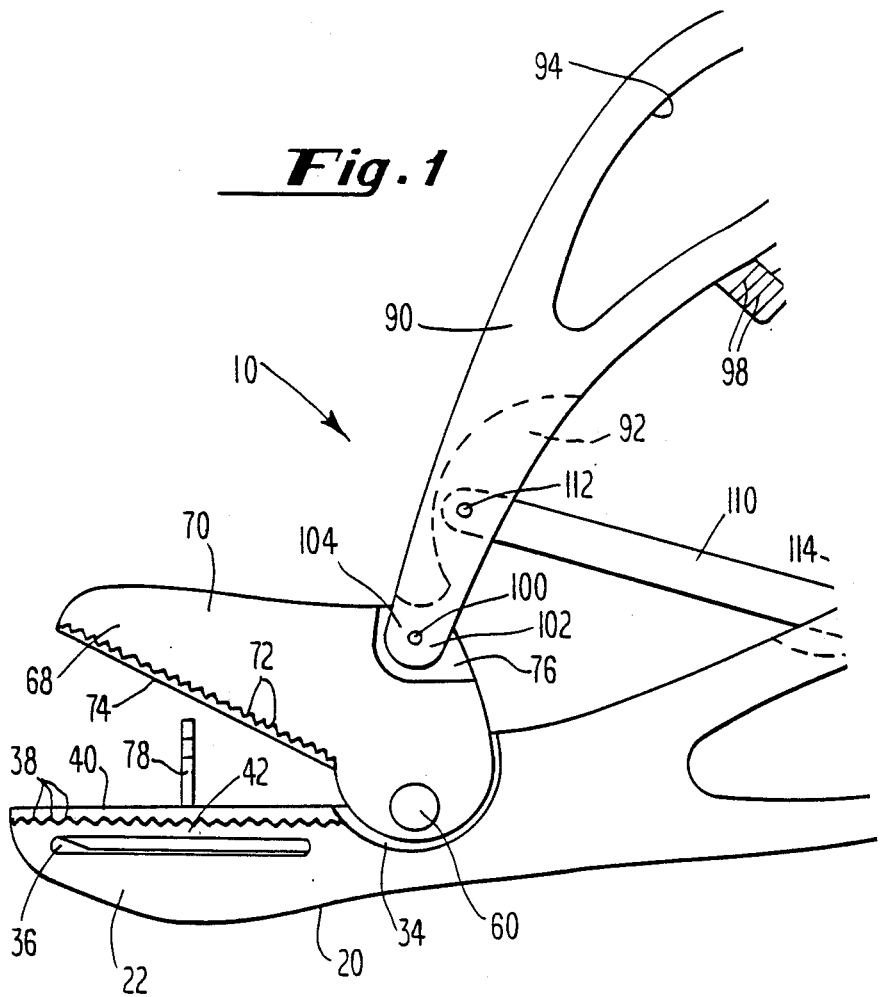
FIG. 1 is an elevational view of a presently preferred embodiment of an umbilical cord cutting and clamping device according to the present invention in an open position viewed from the left or maternal side.

Referring now to the drawings in detail, wherein like reference numerals indicate like elements in each of the several views, reference is first made to FIG. 1, wherein an umbilical cord cutting and clamping device at 10 according to the present invention is illustrated. The device 10 is depicted in FIG. 1 as viewed from the left or maternal side. In the present embodiment the device 10 is adapted to be oriented relative to the umbilical cord to be severed so that the maternal cord end (not illustrated), that is, the end of the umbilical cord connected to the placenta, extends from the side of the device 10 shown in FIG. 1 However, the selection of the left side of the device 10 as the maternal side is arbitrary, and a device according the present invention in which the opposite side of the device is the maternal side can be easily constructed.

The device 10 is preferably constructed of a strong, substantially rigid material which is capable of transmitting sufficient force to cleanly sever the umbilical cord and securely clamp the cord ends. For example, most of the components of the device 10 can be fabricated from a suitable grade of polypropylene by injection molding or a similar process. The device 10 can be manufactured so that it can or should be discarded after a single use, or it can be manufactured in a manner which permits re-use. Preferably, the materials from which the device 10 is fabricated are selected so that the device 10 can be readily sterilized by conventional techniques. The device can be sterilized after manufacture and packaged in a sterile package and discarded after use.

FIG. 1 depicts the device 10 in a fully open position. The device 10 includes a lower assembly 20 including a lower jaw 22 and a lower handle means or lower handle 24, an upper jaw 70, an upper handle 90, and a lower means or bar member 110. The lower jaw 22 includes a lower severing member or lower blade 40 rigidly affixed in the lower jaw 22 by a plurality of fastening members best seen in FIG. 7) and preferably formed from a rigid, sharpenable material such as stainless steel.

As shown in FIG. I, the upper jaw 70 is pivotally affixed to the lower assembly 20 by a fastener 60 extending through apertures (not shown) extending through the upper jaw 70 and the lower assembly 20. The fastener 60 can be a conventional post-and-screw type fastener having a flat headed, cylindrical portion having an interior or female thread and a flat headed male portion adapted to be received by the female portion, the apertures in the upper jaw 70 and the lower assembly 20 being sized to receive and permit rotation of the upper jaw 70 and lower assembly 20 about the cylindrical female portion of the fastener 60. If desired, the apertures in the upper jaw 70 and lower assembly 20 can be counter-sunk to receive the flat heads of the male and female portions of the fastener 60. The fastener 60 thus comprises an upper jaw-lower assembly pivot.

Figure 4:
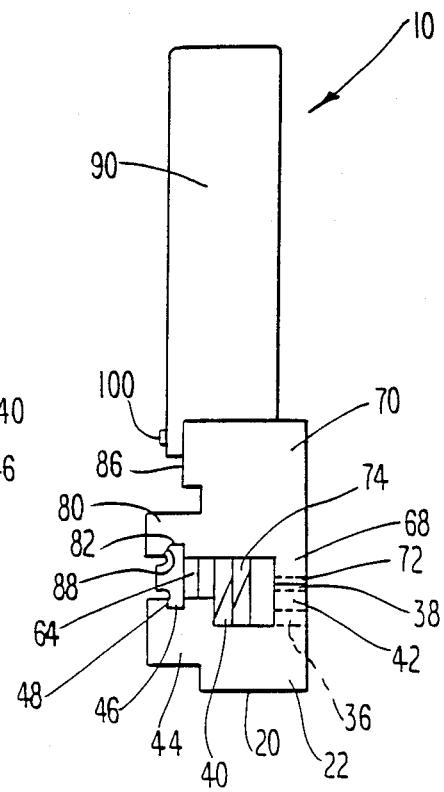
FIG. 4 is a front elevational view of the device of FIG. 1 depicted in the fully closed position.

The upper jaw 70 includes an upper severing member or upper blade 74 rigidly affixed therein by a plurality of fastening means 84 (FIG. 2) and formed from the same material as the lower blade 40. Together the upper severing member 74 and lower severing member 40 cooperate when the device 10 is closed to sever an umbilical cord placed therebetween and thus comprise a severing means. As best seen in FIG. 4, the upper blade 74 and lower blade 40 include forward sections having generally triangular cutting edges adapted to contact and sever the umbilical cord. In addition, the upper blade 74 and lower blade 40 each include rear sections (not shown) provided with apertures for the fastener 60 employed to pivotably affix the upper jaw 70 to the lower assembly 20. Other severing means, such as anvil-type severing means, could also be used.

The lower jaw 22 also includes an integrally formed lower clamping member 42 having a plurality of lower jaw teeth 38 (FIG. 1) formed on the upper surface thereof. Similarly, the upper jaw 70 includes an integrally formed upper clamping member 68 having a plurality of upper jaw teeth 72 formed on the lower surface thereof. The lower clamping member 42 and the upper clamping member 68 cooperate as the device 10 is closed upon an umbilical cord to clamp the severed maternal end of the cord. As best seen in FIG. 4, the upper clamping member 68 and lower clamping member 42 are formed generally parallel to but spaced from the upper blade 74 and lower blade 40 or severing means. Preferably, the lower clamping member 42 and upper clamping member 68, which together comprise a maternal cord end clamping means, are spaced by at least about 3 millimeters from the plane defined by the edges of the upper blade 74 and lower blade 40 as the device 10 is closed. The spacing is believed to facilitate effective clamping of the cut maternal cord end by the upper and lower clamping members 68, 42 to reduce or eliminate bleeding from the cut maternal cord end.

As best seen in FIG. 1 the lower jaw 22 includes an elongated aperture or slot 36 formed adjacent and parallel the lower clamping member 42. This lower jaw aperture 36 serves an important function. As the device 10 is closed on an umbilical cord and the maternal cord end clamping means, that is, the upper clamping member 68 and lower clamping member 42, contact and compress the maternal end of the umbilical cord, the lower jaw aperture 36 permits the lower clamping member 42 to deform to at least partially conform to the exterior surface of the compressed umbilical cord end. This permits a more uniform application of clamping force across the umbilical cord end than would be otherwise possible in the absence of the lower jaw aperture 36.

In prior art scissor-like clamping devices the force applied to the umbilical cord by the prior art device varies inversely with the distance from the pivot or fulcrum of the scissors-like clamping device. At the same time, the extent to which force can be applied to a portion of the umbilical cord by the clamp without tearing or severing the cord is limited. This limiting force can be reached with respect to the portion of the cord closest the fulcrum, while at the same time, the force applied by the prior art clamping device to the portion of the umbilical cord remote from the device fulcrum is insufficient to effectively clamp that portion of the cord against bleeding. The problem is aggravated by the fact that umbilical cords encountered in practice can vary substantially in diameter. Advantageously, the deformation of the clamping means of the device 10 of the present invention permits a more uniform application of force across the cord end to be clamped.

While the device 10 illustrated in the figures has an aperture 36 formed in the lower jaw 22, it is also within the scope of the present invention to provide such an aperture or a similar force distribution means in either the upper jaw 70, or in both the upper jaw 70 and lower jaw 22.

As best seen in FIG. 1, the lower assembly 20 has formed therein a generally flat bottomed recess 34 for receiving a lower rear portion of the upper jaw 70. The aperture (not shown) for receiving the fastener 60 is formed in the recess 34.

The upper handle 90 includes a forward end 102 having a pair of generally flat, generally parallel sides 104, 106 (FIG. 1, FIG. 2) having apertures (not shown) formed therein for receiving a cylindrical pin or pivot 100. The upper jaw 70 has a generally flat recess 76 formed in the left rear upper portion thereof for receiving the left side 104 of the front end 102 of the upper handle 90 while the generally corresponding right upper rear portion of the upper jaw 70 includes a generally flat upper handle mounting surface 86 (FIG. 2) for mounting the right side 106 of the front end 102 of the upper handle 90.

The upper jaw recess 76 and upper handle mounting surface 86 are formed so that the upper handle 90 is generally centered with respect to the severing means. An aperture (not shown) extends through the upper jaw 70 from the upper jaw recess 76 to the upper handle mounting surface 86 for receiving the upper handle-upper jaw pivot 100.

The upper handle 90 also includes an upper handle aperture 94 formed in the rear portion of the upper handle 90 and adapted to permit the upper handle to be comfortably grasped by the fingers or thumb of an operator of the device 10. Similarly, the lower handle 24 includes a lower handle aperture 26 similarly shaped and positioned.

Extending between and pivotably affixed to the upper handle 90 and lower handle 24 is a bar member or lever means or arm 110. As shown in phantom in FIG. 1 the upper handle 90 has a channel like recess 92 formed in the forward lower surface thereof for receiving one end of the lever arm 110. A pivot pin 112 extends through apertures formed in the forward end of the lever arm 112 and the upper handle 90. The upper handle recess 92 is formed so that the lever arm 110 can freely pivot within the recess 92 as the device 10 is opened and closed. Similarly, the lower handle 24 has a channel-like recess 32 formed in the rear upper surface thereof for receiving the other or rear end of the lever arm 110. A second pivot pin 114 extends through apertures (not shown) formed in the lower handle 24 and the end of the lever ar 110, the lower handle recess 32 being formed to permit the lever ar 110 to freely pivot therein as the device 10 is opened and closed.

The axis of rotation of the upper jaw-lower assembly fastener or pivot 60, the lower assembly-lever means pivot 114, the upper handle-lever means pivot 112 and the upper jaw-upper handle pivot 100 are each generally parallel to one another. The distance between the upper jaw-lower assembly pivot 60 and the lower assembly-lever means pivot 114 is greater than the distance between the upper jaw-upper handle pivot 100 and the upper handle-lever means 112. The distance between the lower assembly-upper jaw pivot 60 and the upper jaw upper handle means pivot 100 is less than the distance between the upper handle-lever means pivot 112 and the lower assembly-lever means pivot 114. Thus, as the device 10 is closed, the upper jaw-upper handle pivot 100 moves in an arc about the upper jaw-lower assembly pivot 60. In contrast to prior art scissors-like clamping devices, the present invention is believed to provide a more uniform application of force across the umbilical cord as the umbilical cord is clamped.

A pair of locking tabs 96, 28 are formed on the lower surface of the upper handle 90 and the upper surface of the lower handle 24 respectively for releasably locking together the upper handle 90 and lower handle 24 when the device 10 is closed and an umbilical cord is clamped therein. The locking tabs 96, 28 include a plurality of butress teeth 98, 30 formed on one surface of each and which are adapted to cooperate to lock together the upper handle 90 and lower handle 24 in any one of a plurality of positions selectable by an operator. In the alternative, means for locking the device 10 in a closed position can be otherwise provided. For example, similar locking tabs can be provided proximate the forward ends of the upper jaw 70 and lower jaw 22, or the lever means 110 can be provided with a suitable locking mechanism to the same end. The locking means can be releasable if desired so that the clamping means secured about the maternal cord end can be released after delivery to obtain blood samples or to be separately discarded after inspection of the placenta.

Figure 2:
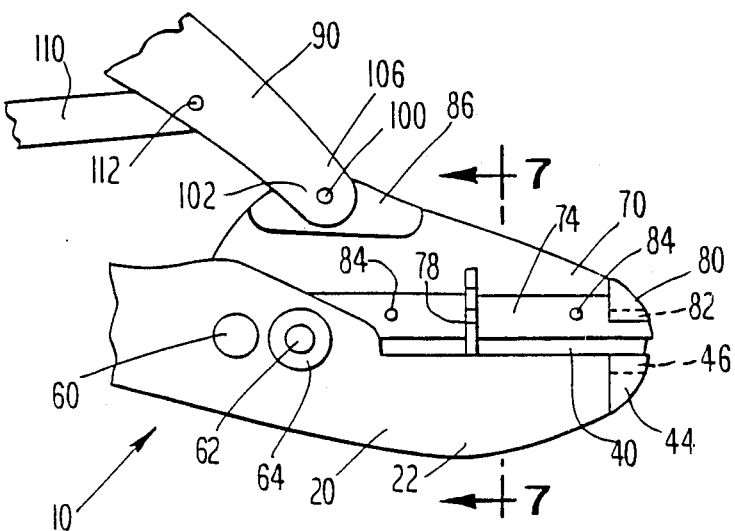
FIG. 2 is a fragmentary elevational view of the device of FIG. 1 showing the device in a fully closed position viewed from the right or fetal side.

As best seen in FIGS. 2 and 4 the upper jaw 70 and lower jaw 22 respectively include opposed clamp support members 80, 44 integrally formed therewith and projecting from the right or fetal side of the device 10 at the forward end thereof. The lower jaw 22 also includes a generally cylindrical stud 62 and a coaxial, generally disc shaped rear clamp support 64 integrally formed therewith and projecting from the right side thereof. The stud 62 and disc 64 together comprise rear support means and the upper clamp support 80 and lower clamp support 44 respectively comprise upper and lower support means for supporting and positioning a detachable fetal cord end clip for use in combination with the device 10.

Figure 3:
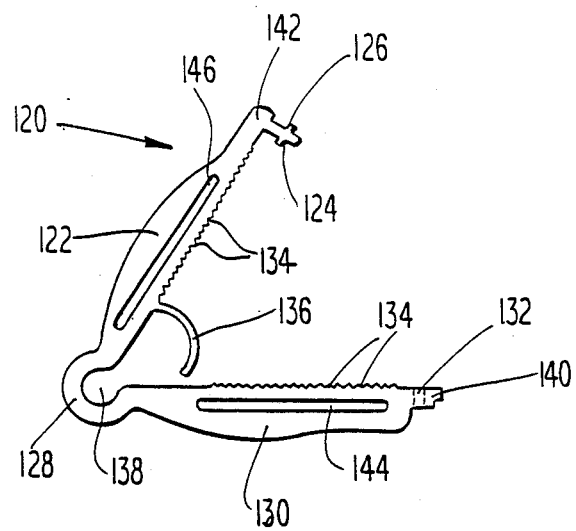
FIG. 3 is an elevational view of a fetal cord end clip for use with the device of FIG. 1 as viewed from the right or fetal side.
Figure 6:
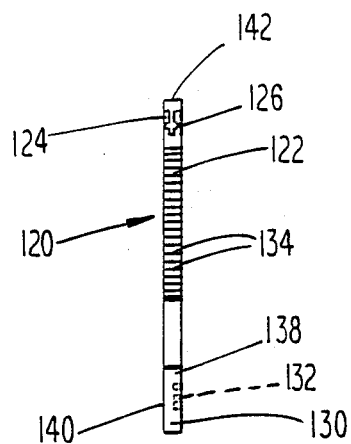
FIG. 6 is a front elevational view of the fetal cord end clip of FIG. 3.

A suitable fetal cord end clamping means or clip 120 is illustrated in FIGS. 3 and 6. The fetal cord end clip 120 includes an arcuate central section 128 having an upper clamp arm 122 and a lower clamp arm 130 extending therefrom. The inner surfaces of the upper clamp arm 122 and lower clamp arm 130 have a plurality of teeth 134 for contacting and gripping the severed fetal end of the umbilical cord. Each clamp arm 122, 130 has formed therein an elongated aperture 144, 146 to provide a cushioning effect when the clip 120 is closed upon a fetal cord end. A locking tab 124 is provided proximate the end 142 of the upper clamp arm 122 opposite the central section 128. The locking tab 124 has a pair of protrusions or projections 126 extending in the plane defined by the clamp arms 122, 130. A lock aperture 132 is formed in the end 140 of the lower clamp arm 130 opposite the central section 128. The locking tab 124 is sized and positioned to be securely received when the clamp 120 is closed by the lock aperture 132, the pair of protrusions 126 defining a lock position for the clamp 120. The central section 128 is generally arcuate and has formed therein a generally arcuate opening or aperture 138 adapted to mount the central section 128 of the clip 120 on the stud 62 of the lower jaw 22 of the device 10. As the aperture 138 becomes smaller as the clamp 120 is compressed, the mounting stud 62 should have a diameter slightly less than the aperture 138 when the clamp 120 is compressed.

The lower clamp arm end 140 and the upper clamp arm end 142 have generally flat outer surfaces adapted to contact and be received by the lower clamp support 44 and upper clamp support 80 respectively of the cutting and clamping device 10. The fetal cord end clip 120 is preferably formed from a sterlizable substantially rigid but somewhat deformable material such as a suitable grade of polypropylene, high density polyethylene, or the like. As shown in FIG. 3 the generally flat upper clamp arm 122 and lower clamp arm 130 form an acute angle with respect to one another when the clip is in a relaxed and uncompressed state. The generally arcuate central or spring section 128 of the clip 120 functions as a spring member to oppose forces tending to close the clip 120 shut. The upper clamp arm 122, the lower clamp arm 130 and the central section 128 are generally flat and lie in a single plane, as best seen in FIG. 6. The clip 120 also includes an elongated arcuate cord positioning arm 136 extending perpendicularly from the inside surface of the upper clamp arm 122.

Figure 5:
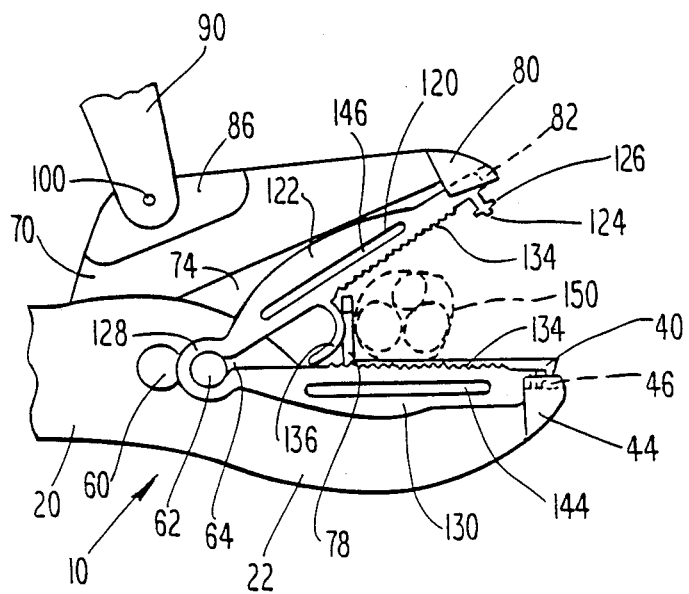
FIG. 5 is a fragmentary right side elevational view of the device of FIG. 1 in the fully opened position and having mounted therein the fetal cord end clip shown in FIG. 3.

FIG. 5 depicts a fragmentary right side elevational view of the device 10 having mounted therein a fetal cord end clip 120. The clip 120 must be compressed slightly to mount the clip 120 in the device 10 when the device 10 is in the fully opened position. The central section 128 of the clip 120 is placed over the stud 62 and is spaced from the side of the lower jaw 22 by the disc-like rear clamp support 64. The lower clamp arm end 140 is positioned in a recess or slot 46 formed in the upper surface of the lower clamp support 44 and the upper clamp arm end 142 is positioned in a respective recess or slot 82 formed in the lower surface of the upper clamp support 80. As best seen in FIG. 4 both the lower slot 46 and the upper slot 82 has an inner wall which is slanted generally parallel to the cutting plane of the cord severing means.

In addition, the lower slot 46 has a bottom wall and the upper slot has a "bottom" (more accurately top) wall which are generally perpendicular to the inner walls of the respective slots, the bottom and top walls being adapted to contact the outer surfaces of the lower clamp arm end 140 and upper clamp arm end 142 respectively. The upper slot 82 has an outer wall 88, extending from the top wall at an obtuse angle, preferably about 135°, and adapted to facilitate ejection of a fetal cord end clip 120 closed about a fetal cord end. If desired, the lower slot 46 can also be provided with an outer wall 48 which extends at an obtuse angle. The upper slot 82, the lower slot 46 and the rear clamp support 64 are formed so that a fetal cord end clip 120 mounted in the device 10 is oriented generally parallel to but spaced from the severing means. Preferably, the fetal cord end clip 122 is so spaced such that the distance between the inner surface of the fetal cord end clip 120 and the outer surface of the lower blade 40 is at least about 3 millimeters.

The spacing between the fetal cord end clip 120 and the severing means is believed to promote secure clamping of the fetal cord end and to reduce the likelihood of post clamping bleeding therefrom.

As shown in phantom in FIG. 5 the umbilical cord 150 is placed adjacent the cord positioning arm 136 of the fetal cord and clamp 120 when the device 10 is in the open position. Subsequently, the operator manually closes the clamping device 10 by simultaneously grasping and bringing together the upper handle 90 and lower handle 24, the upper handle 90 pivoting on the lever arm 120 to force the upper jaw 70 towards the lower jaw 22 and to simultaneously sever the umbilical cord 150 and clamp the maternal cord end between the upper and lower clamping members 68, 42 of the device 10 and the fetal cord end between the upper and lower clamp arms 122, 130 of the fetal cord end clip 120.

As best seen in FIG. 5, the lower jaw 70 includes an elongated, generally vertically oriented ejecting member 78 which is positioned to contact the inner surface of the upper clamp arm 122 and to displace the upper clamp arm end 142 from the upper slot 82 after the upper and lower clamp arms 122, 130 have been locked together about the fetal cord end.

Figure 7:
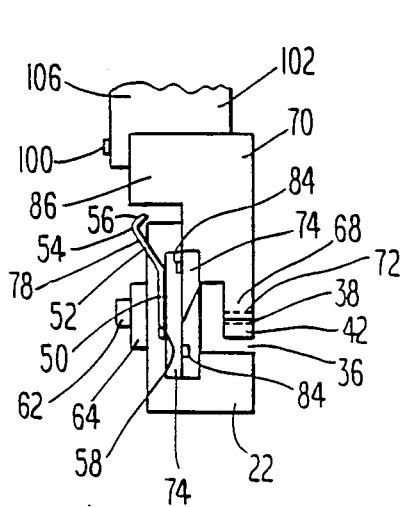
FIG. 7 is a fragmentary elevational sectional view of the device of FIG. 2 taken along the line 7—7.

As best seen in FIG. 7, the ejecting member 78 includes a generally vertical bottom or lower section 50, a middle section 52 which protrudes outwardly toward the plane in which the fetal cord end clip 120 lies when it is mounted in the device 10, and an upper section 56, oriented back toward the longitudinal plane of the device 10. A contact surface 54 is formed between the middle section of 52 and the upper section 56 for contacting and ejecting the upper clamp arm 142 of the clip 120. The ejecting member 78 is mounted between the lower jaw 22 and the lower blade 40 in a recess 58 formed in the lower jaw 22. Alternatively, the ejecting member 78 can be formed integrally with the lower jaw 22 or with the lower blade 40.

As the fetal cord end clip 120 is closed about the umbilical cord 150 the upper clamp arm 122 is deformed and displaced in the direction of the ejecting member 78. Eventually the upper clamp arm 122 contacts the contact surface 54 of the ejecting member 78. The obtuse angle between the outer wall 88 and top wall of the upper slot 82 of the upper clamp support 80 is selected to cooperate with the ejecting member 78 to permit ejection of the upper clamp arm end 142 from the upper slot 82 after the fetal cord end clip 120 has been locked. After the lower clamp arm end 142 has been ejected and the device 10 has been closed and locked on the maternal cord end, the fetal cord end clip 120 clamped about the fetal cord end is released from the device 10 simply by moving apart the fetal cord end cutting and clamping device 10 and the fetal cord end clip 120.

Various modifications can be made in the details of the embodiments of the umbilical cord cutting and clamping device 10 and fetal cord end clip 120 of the present invention, all within the spirit and scope of the invention as defined by the appended claims.

I claim:

1. An umbilical cord cutting and clamping device for severing an umbilical cord to form a maternal cord end and a fetal cord end and for clamping the maternal cord end and the fetal cord end, the device being adapted for use with a fetal cord end clip which is detachable from the device, the device comprising:

a lower assembly including a lower jaw and lower handle means the lower jaw including a lower clamping member for clamping the maternal end, a lower severing member for severing the umbilical cord, and lower support means for supporting and positioning the fetal cord end clip, the lower clamping member being unitary with the lower jaw;

an upper jaw including an upper clamping member for clamping the maternal cord end, an upper severing member for severing the umbilical cord, and support means for supporting and positioning the fetal cord end clip, the upper clamping member being unitary with the upper jaw; the upper jaw being pivotably affixed to the lower assembly and adapted to be pivoted from an open position for admitting an umbilical cord between the upper jaw and the lower jaw and a closed position for severing and clamping the cord;

an upper handle means pivotably affixed to the upper jaw; and lever means pivotably affixed to the upper handle means and the lower handle means, the distance between the upper jaw-lower assembly pivot and the lower assembly-lever means pivot being greater than the distance between the upper jaw-upper handle means pivot and the upper handle-lever means pivot and the distance between the lower assembly-upper jaw pivot and the upper jaw-upper handle means pivot being less than the distance between the upper handle means-lever means pivot and the lower assembly-lever means pivot, so as the device is closed the upper jaw-upper handle pivot moves in and arc about the jaw-lower assembly pivot.

2. A device according the claim 1 wherein the lower jaw is adapted to deform as the maternal cord end is clamped to conform to the clamped maternal cord end.

3. A device according to claim 2 wherein an elongated aperture formed in the lower jaw, the aperture being sized and positioned to allow the lower jaw clamping to deform as a maternal cord end is clamped as the device is closed, the lower jaw having first and second generally parallel sides, the aperture extending from the first side of the lower jaw through the lower jaw to the second side of the lower jaw and being open to the atmosphere.

4. A device according to claim 1 wherein the lower severing member and the upper severing member comprise a severing means cooperating to sever an umbilical cord positioned therebetween when the device is closed, the upper clamping member and lower clamping member comprising a maternal cord end clamping means and cooperating to clamp the maternal cord end, and the maternal cord end clamping means being generally parallel and spaced from the severing means.

5. A device according to claim 4 wherein the clamping means is spaced by at least about 3 millimeters from the severing means.

6. A device according to claim 1 wherein the upper and lower support means comprise means for supporting and positioning a fetal cord end clip when the device is open and as the device is closed and the fetal cord end is clamped, the device further including means for releasing the fetal cord end clip from the device as the device is closed and after the fetal cord end has been clamped.

7. A device according to claim 6 wherein the release means comprises a cam member.

8. A device according to claim 7 wherein the lower jaw has the cam member formed integrally therewith.

9. A device according to claim 6 wherein the upper and lower severing members comprise a severing means, the support members being adapted to position the fetal cord end clip generally parallel to and spaced from the severing means.

10. A device according to claim 9 wherein the fetal cord end clip means is spaced at least about 3 millimeters from the severing means.

11. A device according to claim 10 wherein the support means includes a rear support member for the central section of the fetal cord end clip, a lower support member for a first clamping arm of the fetal cord end clip, and an upper support member for a second clamping arm of the fetal cord end clip.

12. A device according to claim 11 wherein the lower assembly includes the rear support member and the lower support member, the upper jaw including the upper support member.

13. A device according to claim 12 wherein the lower assembly includes spacing means proximate the rear support means for spacing the central section of the fetal cord end clip from the severing means.

14. A device according to claim 13 wherein in the upper and lower support means include slots for receiving an positioning the first and second clamping arms of the fetal cord end clip the slots being generally parallel to and spaced from the severing means, the slots having bottom walls for contacting the clamping arms of the clip opposite the interfaces of the clamping arms, first interior walls proximate the severing means and generally perpendicular to the bottom walls, and second interior walls extending at an obtuse angle from the respective bottom wall.

15. A device according to claim 14 wherein the obtuse angle is about 135 degrees.

16. A device according to claim 9 wherein the support means is adapted to support a fetal cord end clamping means having a pair of elongated arms extending radially from a generally arcuate central section having an aperture formed therein, each arm having a generally straight inner surface having teeth formed thereon and lock means formed proximate the end thereof for locking together the arms when the clamping means is closed, the aperture being formed in the central section for receiving a support member, the arms of the open clamping means forming an acute angle.

17. A device according to claim 1 wherein the lower jaw and lower handle means are unitary.

18. In combination, an umbilical cord cutting and clamping device for severing an umbilical cord to form a maternal cord end and a fetal cord end and for clamping the maternal cord end and the fetal cord end, and a fetal cord end clip which is detachable from the device, the device comprising:

a lower assembly including a lower jaw and lower handle means the lower jaw including a lower clamping member for clamping the maternal end, a lower severing member for seering the umbilical cord, and lower support means for supporting and positioning the fetal cord end clip, the lower clamping member being unitary with the lower jaw;

an upper jaw including an upper clamping member for clamping the maternal cord end, an upper severing member for severing the umbilical cord, and support means for supporting and positioning the fetal cord end clip, the upper clamping member being unitary with the upper jaw; the upper jaw being pivotably affixed to the lower assembly and adapted to be pivoted from an open position for admitting an umbilical cord between the upper jaw and the lower jaw and a closed position for severing and clamping the cord;

an upper handle means pivotably affixed to the upper jaw; and lever means pivotably affixed to the upper handle means and the lower handle means, the distance between the upper jaw-lower assembly pivot and the lower assembly-lever means pivot being greater than the distance between the upper jaw-upper handle means pivot and the upper handle-lever means pivot and the distance between the lower assembly-upper jaw pivot and the upper jaw-upper handle means pivot being less than the distance between the upper handle means-lever means pivot and the lower assembly-lever means pivot, so as the device is closed the upper jaw-upper handle pivot moves in and arc about the jaw-lower assembly pivot.

19. A combination according to claim 18 further including means for positioning an umbilical cord, the positioning means comprising an elongated arcuate cord positioning arm formed integrally with the fetal cord end clip and extending from the interior surface of a clamping arm thereof and spaced from the central section of the fetal cord end clip.

20. A combination according to claim 18 wherein the lower jaw and lower handle means are unitary.

* * * * *